United States Patent

Marks et al.

[11] Patent Number: 5,854,166
[45] Date of Patent: Dec. 29, 1998

[54] SYNTHESIS AND USE OF (PERFLUOROARYL) FLUORO-ALUMINATE ANION

[75] Inventors: Tobin J. Marks, Evanston; You-Xian Chen, Chicago, both of Ill.

[73] Assignee: Northwestern University, Evanston, Ill.

[21] Appl. No.: 912,617

[22] Filed: Aug. 18, 1997

[51] Int. Cl.$^6$ .............................. B01J 31/00; C07F 5/00; C07F 17/00; C08F 4/44

[52] U.S. Cl. .................... 502/153; 502/103; 502/117; 502/102; 502/104; 534/11; 526/127; 526/160; 526/943; 526/346; 526/351; 526/352; 556/27; 556/28; 556/53; 556/187

[58] Field of Search .................... 502/102, 103, 502/117, 153; 534/11, 15; 526/127, 160, 943; 556/27, 28, 43, 53, 58, 187

[56] References Cited

U.S. PATENT DOCUMENTS

| | | | |
|---|---|---|---|
| 3,928,303 | 12/1975 | Yasui et al. | 260/94.3 |
| 5,066,741 | 11/1991 | Campbell, Jr. | 526/171 |
| 5,391,661 | 2/1995 | Naganuma et al. | 526/133 |
| 5,599,761 | 2/1997 | Turner | 502/152 |
| 5,602,269 | 2/1997 | Biagini et al. | 556/170 |
| 5,728,816 | 3/1998 | Garbassi et al. | 534/15 |
| 5,734,010 | 3/1998 | Sommazzi et al. | 502/103 |
| 5,763,549 | 6/1998 | Elder et al. | 502/117 |

FOREIGN PATENT DOCUMENTS 0 427 697 B1  5/1991  European Pat. Off. .
0 573 403 A2  12/1993  European Pat. Off. .

OTHER PUBLICATIONS

Chen et al., Very Large Counteranion Modulation of Cationic Metallocene Polymerization Activity and Stereoregulation by a Sterically Congested (Perfluoroaryl) fluoroaluminate, J. Am. Chem. Soc., 1997, vol. 119, pp. 2582–2583.

Jordan et al., *J. Am. Chem. Soc.*, vol. 108, pp. 1718–1719 (1986).

Marks, Tobin J., Surface–Bound Metal Hydrocarbyls. Organometallic Connections between Heterogeneous and Homogeneous Catalysts, *Accounts of Chemical Research*, vol. 25, No. 2, pp. 57–65, Feb., 1992.

Yang et al., Cationic Zirconocene Olefin Polymerization Catalysts Based on the Organo–Lewis Acid Tris(pentafluorophenyl)borane. A Synthetic, Structural, Solution Dynamic, and Polymerization Catalytic Study, *J. Am. Chem. Soc.* 116, 10015–10031, 1994.

Chen et al., Organo–Lewis Acids As Cocatalysts in Cationic Metallocene Polymerization Catalysts. Unusual Characteristics of Sterically Encumbered Tris(perfluorobiphenyl)borane, *J. Am. Chem. Soc.*, 118, pp. 12451–12452, 1996.

*Primary Examiner*—Mark L. Bell
*Assistant Examiner*—J. Pasterczyk
*Attorney, Agent, or Firm*—Welsh & Katz, Ltd.

[57] ABSTRACT

A trityl perfluorophenyl alumninate such as tris(2,2',2"-nonafluorobiphenyl) fluoroaluminate (PBA$^-$) and its role as a cocatalyst in metallocene-mediated olefin polymerization is disclosed.

11 Claims, 2 Drawing Sheets

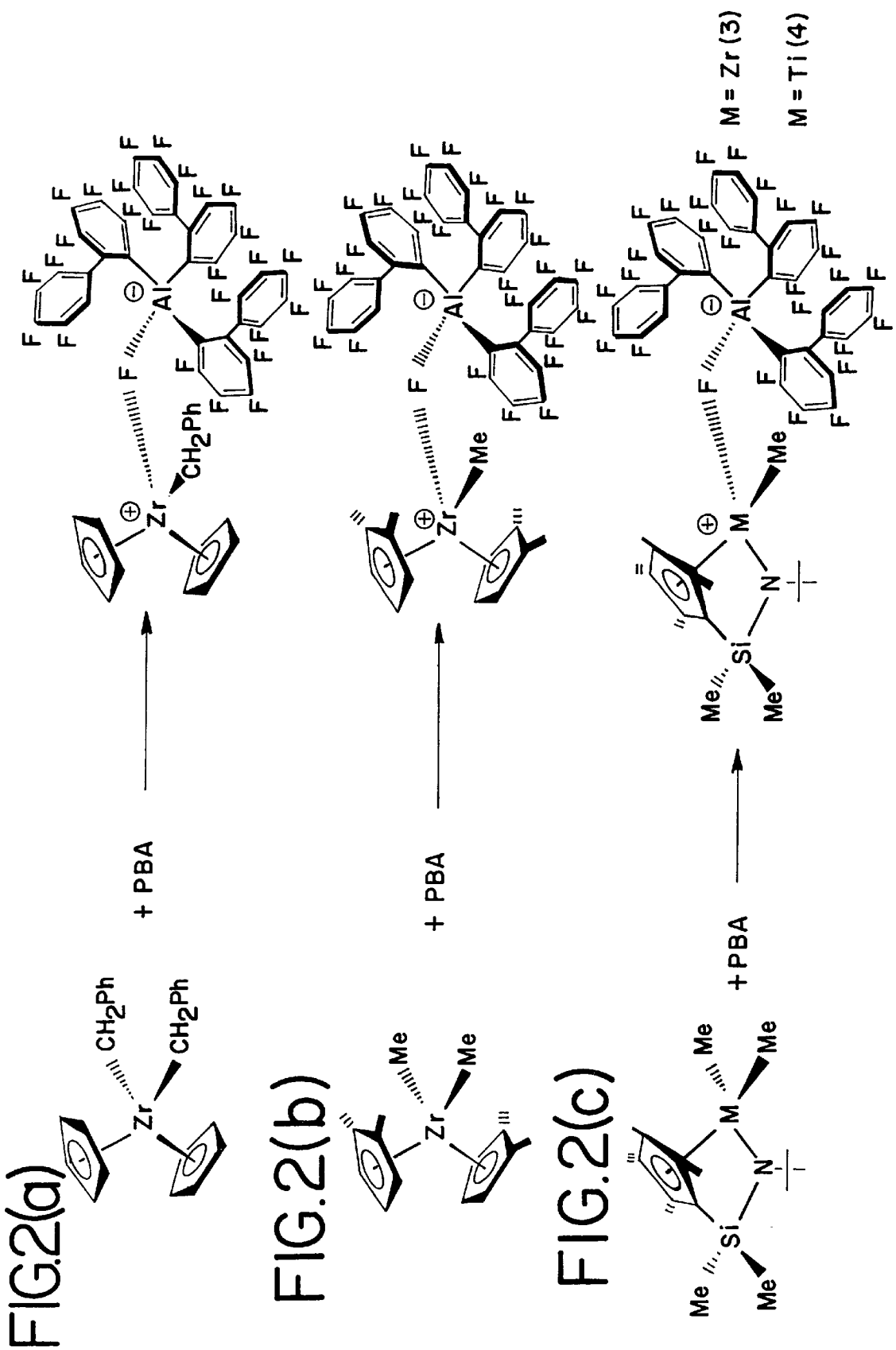

SYNTHESIS AND USE OF (PERFLUOROARYL) FLUORO-ALUMINATE ANION

This invention was made with Government support under Contract No. DE-FG02-86ER13511 awarded by the Department of Energy. The Government has certain rights in this invention.

This is a non-provisional application, from provisional application Ser. No. 60/024,190, filed Aug. 19, 1996.

BACKGROUND OF THE INVENTION

This invention relates to the compositions of matter useful as a catalyst system, to a method for preparing these catalyst systems and to a method for polymerization utilizing the catalyst system.

The use of soluble Ziegler-Natta type catalysts in the polymerization of olefins is well known in the prior art. In general, such systems include a Group IV-B metal compound and a metal or metalloid alkyl cocatalyst, such as aluminum alkyl cocatalyst. More broadly, it may be said to include a mixture of a Group I-III metal alkyl and a transition metal complex from Group IVB-VB metals, particularly titanium, zirconium, or hafnium with aluminum alkyl cocatalysts.

First generation cocatalyst systems for homogeneous metallocene Ziegler-Natta olefin polymerization, alkylaluminum chlorides ($AlR_2Cl$), exhibit low ethylene polymerization activity levels and no propylene polymerization activity. Second generation cocatalyst systems, utilizing methyl aluminoxane (MAO), raise activities by several orders of magnitude. In practice however, a large stoichiometric excess of MAO over catalyst ranging from several hundred to ten thousand must be employed to have good activities and stereoselectivities. Moreover, it has not been possible to isolate characterizable metallocene active species using MAO. The third generation of cocatalyst, $B(C_6F_5)_3$, proves to be far more efficient while utilizing a 1:1 catalyst-cocatalyst ratio. Although active catalyst species generated with $B(C_6F_5)_3$ are isolable and characterizable, the anion $MeB(C_6F_5)_3^-$ formed after $Me^-$ abstraction from metallocene dimethyl complexes is weakly coordinated to the electron-deficient metal center, thus resulting in a decrease of certain catalytic activities. The recently developed $B(C_6F_5)_4^-$ type of non-coordinating anion exhibits some of the highest reported catalytic activities, but such catalysts have proven difficult to obtain in the pure state due to poor thermal stability and poor crystallizability, which is crucial for long-lived catalysts and for understanding the role of true catalytic species in the catalysis for the future catalyst design. Synthetically, it also takes two more steps to prepare such an anion than for the neutral organo-Lewis acid.

SUMMARY OF THE INVENTION

Accordingly, it is an object of the subject invention to prepare and utilize a new class of olefin polymerization catalytic system.

A further object of the subject invention is a catalytic system which permits better control over molecular weight, molecular distribution, stereoselectivity, and comonomer incorporation.

Another object of the subject invention is a Ziegler-Natta type catalytic system which reduces the use of excess cocatalyst and activates previously unresponsive metallocenes.

These and other objects are attained by the subject invention whereby in one embodiment, a strong organo-Lewis acid, such as a (perfluoroaryl)aluminate anion and in particular tris(2,2',2" nonafluorobiphenyl)fluoroaluminate ($PBA^-$) is utilized as a highly efficient cocatalyst for metallocene-mediated olefin polymerization. $PBA^-$ exhibits higher catalytic activities and can activate previously unresponsive metallocenes. The synthesis of the stable perfluoroaryl aluminum anion, tris(2,2',2"-nonafluorobiphenyl) fluoroaluminate ($PBA^-$) is accomplished with the use sterically encumbered perfluorobiphenyl ligand.

In one embodiment of the subject invention a strong organo-Lewis acid, such as a fluoraryl metal compound, is utilized to synthesize stoichiometrically precise, isolable/crystallographically characterizable, highly active "cation-like" metallocene polymerization catalysts.

In the subject application, "Cp" represents a cyclopentadienyl radical which may be substituted or unsubstituted, and:

(Cp)(Cp') or Cp-A-Cp' and Cp and Cp' are the same or different cyclopentadienyl ring substituted with zero to five substituent groups $\beta$ and each substituent group $\beta$ is, independently, a radical which can be hydrocarbyl, substituted-hydrocarbyl, halocarbyl, substituted-halocarbyl, hydrocarbyl-substituted organometalloid, halocarbyl-substituted organometalloid, or halogen radicals (the size of the radicals need not be limited to maintain catalytic activity; however, generally the radical will be a $C_1$ to $C_{20}$ radical) or Cp and Cp' are a cyclopentadienyl ring in which any two adjacent R groups are joined forming a $C_4$ to $C_{20}$ ring to give a saturated or unsaturated polycyclic cyclopentadienyl ligand such as indenyl, tetrahydroindenyl, fluorenyl, or octahydrofluorenyl and A is a bridging group which restricts rotation of the two Cp-groups.

Each carbon atom in the cyclopentadienyl radical ("Cp") may be, independently, unsubstituted or substituted with the same or different radical group which is a hydrocarbyl, substituted-hydrocarbyl, halocarbyl, substituted-halocarbyl hydrocarbyl radicals in which adjacent substituents are joined to form a ring of 4 to 10 or more carbon atoms, hydrocarbyl- and halocarbyl-substituted organometalloid radicals and halogen radicals.

More specifically, a fluoroaryl metal compound such as $ER'R''R'''F^-$ reacts with early transition metal or actinide alkyls to yield highly reactive cationic complexes:

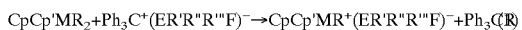

where=cyclopentadienyl, cyclopentadienyl substituted or bridged

CpCp' cyclopentadienyl ligands such as CpACp', indenyl Cp, allyl Cp, benzyl Cp; substituted indenyl Cp; substituted allyl Cp; substituted benzyl Cp; $\eta^5$-1,2-$Me_2C_5H_3;\eta^5$-1,3-$(SiMe_3)_2C_5H_3;\eta^5$-$C_5Me_5$;($^t$BuN)$Me_2Si(\eta^5$-$Me_4C_5)$ M=early transition metal or actinide, e.g., Ti, Zr, Hf, Th, U R=$PhCH_2$, alkyl or aryl group (C$\leq$20), hydride R', R", R'''=fluorinated phenyls, fluorinated biphenyl or fluorinated polycyclic fused ring groups E=Al, Ga, In As a specific example of the above, the reaction of $PBA^-$ with a variety of zirconocene dimethyl complexes proceeds rapidly and quantitatively to yield, after recrystallization from hydrocarbon solvents, in the catalytic complex set forth in Eq. 2.

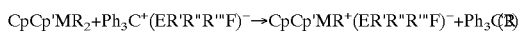

Such catalytic complexes have been found to be active homogeneous catalysts for (α-olefin polymerization.

The cocatalyst of the subject invention may be referred to as $ER_F'R_F''R_F'''F^-$; where R', R" and R'" represent at least one and maybe more fluorinated biphenyls or other fluorinated polycyclic groups, such as naphthyl. Two of the biphenyls may be substituted with a phenyl or other aryl group. Both the biphenyls and the phenyl groups should be highly fluorinated, preferably with only one or two hydrogens on a group, and most preferably, as in PBA$^-$ with no hydrogens and all fluorines. E represents Al, Ga or In.

BRIEF DESCRIPTION OF THE DRAWINGS

The cocatalyst system of the subject invention can be better understood with reference to the drawings wherein:

FIGS. 2a, 2b and 2c each show the reaction pathway for a catalyst system according to the subject invention.

DETAILED DESCRIPTION OF THE INVENTION

Figure 1:
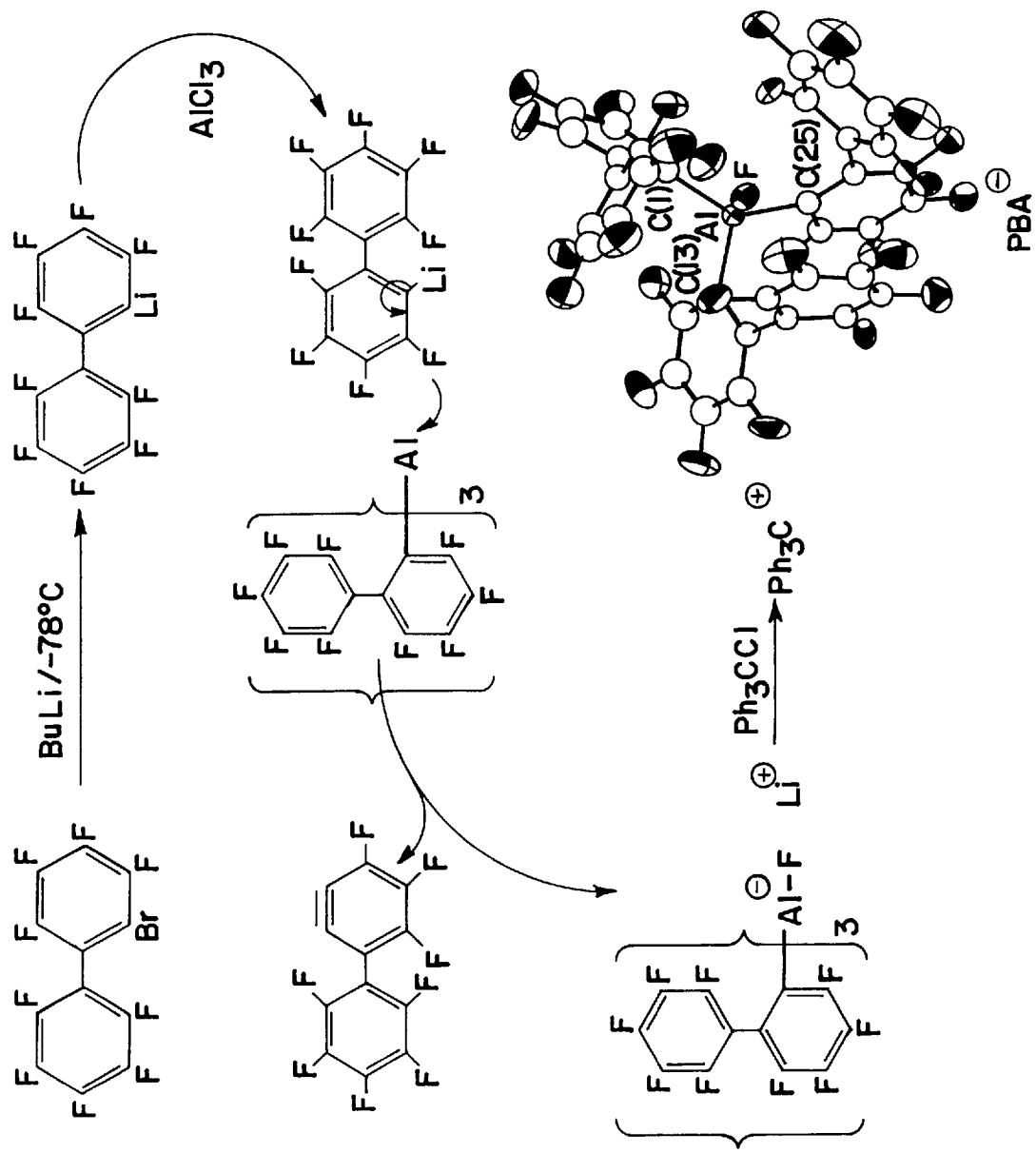
FIG. 1 is a reaction pathway for the synthesis of PBA$^-$.

Under a variety of reaction conditions and ratios of reagents, the reaction of 2-nonafluorobiphenyl lithium and AlCl$_3$ all appear to lead to the formation of a compound with the formula Ar$^F_3$F Al$^-$Li$^+$, resulting from fluoride abstraction by the strongly Lewis acidic trisperfluoro-biphenyl aluminum species generated in situ (FIG. 1). Ion exchange metathesis of this lithium salt with Ph$_3$CCl results in the formation of stable trityl perfluorobiphenyl aluminate (PBA$^-$). The structure of PBA$^-$ has been characterized by X-ray diffraction and shows a non-associated trityl cation and aluminate anion.

Isolation and Characterization of Cationic Group 4 Complexes Derived from PBA

The reaction of PBA$^-$ with various metallocene dialkyls readily generates the corresponding cationic complexes (FIGS. 2a–2c). The PBA$^-$ anion is weakly coordinated to the metal center via F$^-$ bridges in these complexes. This coordination is evident from the large downfield shift ($\geq 30$ ppm) of the Al—F F resonance in the $^{19}$F NMR as compared to that of free PBA. This coordination lowers the symmetry of the cation portion as well. Furthermore, the coordinated anion is chiral. The relatively stable chirality of the anion stems from the bulkiness of the molecule which suppresses the rotation of perfluoroaryl rings and renders the geometry fixed, resulting in nine (9) sets of characteristic resonances in the $^{19}$F NMR. The influence of the anion chirality on the cation portion can be observed spectroscopically. In the reaction product of FIG. 2a, there are two diastereotopic CH$_2$Ph protons with $^2$J value of 11.4 Hz and two magnetically nonequivalent Cp rings, which reflects the chiral environment of the coordinated anion.

With diastereotopic ring substitution in the metallocene, the structure of the reaction product shown in FIG. 2b offers unique NMR probes for a better understanding of the molecular structure. Coordination of an achiral anion such as CH$_3$B(C$_6$F$_5$)$_3^-$ to the metal center of the cation portion of FIG. 2b results in the observation of two diastereotopic Cp methyls and three types of Cp ring protons having different chemical shifts. However, in the reaction product of FIG. 2b with a coordinated chiral anion, all the Cp methyls (four types) and Cp ring protons (six types) have different chemical shifts, clearly indicating the chiral induction of the anion.

Constrained geometry catalysts (FIG. 2c) activated by PBA exhibit two distinct silyl methyls and four different Cp methyls. The structure of the reaction product of FIG. 3c has been characterized by X-ray diffraction and reveals a chiral PBA$^-$ anion coordinated via an F-bridge with Zr—F and Al—F bond lengths of (2.123) and (6) Å, respectively. The Zr—CH$_3$ of bond distance of 2.21(1) Å is almost identical to that in (CGC)Zr(Me)[MeB(C$_6$F$_5$)$_3$] (2.224 (5)) Å, reflecting the cationic character of the zirconium center. In cases where the bulkiness of cationic portion is increased, thereby pushing the anion away from the coordinative periphery, the product formed from the reaction appears neither stable nor isolable, e.g., [(C$_5$Me$_5$)$_2$ZrMe$_2^+$ PBA$^-$]. However, this distant contact cation-anion pair exhibits extremely high activity for olefin polymerization when generated in situ.

Ph$_3$C$^+$PBA$^-$ has been synthesized in essentially quantitative yields as compared to the 30–50% yields experienced with B(C$_6$F$_5$)$_3$, currently a very important Lewis acidic cocatalyst in the polyolefin industry. More particularly, reaction of PBA$^-$ with group 4 methyls proceeds cleanly to yield cationic complexes such as set forth below.

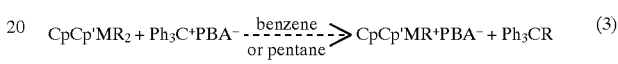
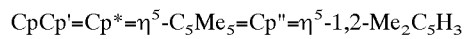

$$CpCp'MR_2 + Ph_3C^+PBA^- \xrightarrow[\text{or pentane}]{\text{benzene}} CpCp'MR^+PBA^- + Ph_3CR \quad (3)$$

CpCp'=Cp*=$\eta^5$-C$_5$Me$_5$=Cp"=$\eta^5$-1,2-Me$_2$C$_5$H$_3$

M=Ti, Zr, Hf

R=PhCH$_2$, CH$_3$, alkyl or aryl group with C$\leq$20; hydride

CpCp'MR$^+$PBA$^-$ may be any cyclopentadienyl, substituted cyclopentadienyl or bridged cyclopentadienyl complex paired with PBA$^-$, such as Cp$_2$ZrCH$_2$Ph$^+$ PBA$^-$; Cp$_2$ZrH$_3^+$PBA$^-$; Cp$_2$"ZrCH$_3^+$PBA$^-$; (1,3-(Si, Me$_3$)$_2$C$_5$H$_3$)$_2$ZrCH$_3^+$PBA$^-$; Cp'$_2$ZrCH$_3^+$PBA$^-$; (CGC)ZrCH$_3^+$PBA$^-$; (CGC)TiCH$_3^+$PBA$^-$; and rac-Me$_2$Si(Ind)$_2$ZrCH$_3^+$PBA$^{31}$ (CGC=$^t$BuN Me$_2$Si($\eta^5$-Me$_4$C$_5$); (Ind=$\eta^5$-C$_9$H$_6$), 2-methyl (Ind) ZrCH$_3^+$PBA$^{31}$; (CpZrCp'Zr)$_2$ ZrCH$_3^{30}$PBA$^{31}$.

For polymerization of olefin monomers, catalytic activities of the cations generated from PBA$^-$ can be greater than those of monomeric cations generated from B(C$_6$F$_5$)$_3$ in cases of bulky L and L' ligands presumably because PBA$^-$ functions as a non-coordinating anion as compared to the weakly coordinating anion MeB(C$_6$F$_5$)$_3$. Polymerization reactions show very high activities for α-olefin polymerization, and identify PBA$^-$ to be a truly non-coordinating anion. When polymerizing α-olefins larger than ethylene and particularly propylene and styrene, high isotacticity can be observed.

Experimental

Materials and Methods.

All manipulations of air-sensitive materials were performed with rigorous exclusion of oxygen and moisture in flamed Schlenk-type glassware on a dual-manifold Schlenk line or interfaced to a high-vacuum line (10$^{-6}$ Torr), or in a nitrogen-filled vacuum atmospheres glovebox with a high capacity recirculator (1–2 ppm O$_2$). Argon (Matheson, prepurified) and ethylene (Matheson, polymerization grade) were purified by passage through a supported MnO oxygen-removal column and an activated Davison 4A molecular sieve column. Ether solvents were purified by distillation from Na/K alloy/benzophenone ketyl. Hydrocarbon solvents (toluene, pentane) were distilled under nitrogen from Na/K alloy. All solvents for vacuum line manipulations were stored in vacuo over Na/K alloy in Teflon-valved bulbs. Deuterated solvents were obtained from Cambridge Isotope Laboratories (all$\geq$99 atom %D) and were freeze-pump-thaw degassed and dried over Na/K alloy and stored in resealable flasks. Non-halogenated solvents were dried over Na/K alloy and halogenated solvents were distilled over $P_2O_5$ and stored over activated Davison 4 Å molecular sieves. $BrC_6F_5$ (Aldrich) was vacuum distilled over $P_2O_5$. $AlCl_3$, $Ph_3CCl$ and BuLi (1.6M in hexanes) were purchased from Aldrich. The zirconocene and titanocene complexes $Cp_2ZrMe_2$; $Cp_2Zr(CH_2Ph)_2$; $(1,2\text{-}Me_2C_5H_3)_2ZrMe_2$; $[1,3\text{-}(SiMe_3)_2C_5H_3]_2ZrMe_2$ $(C_5Me_5)_2ZrMe_2$, $Me_2Si(Me_4C_5)$ ($^tBuN$) $ZrMe_2$ and $Me_2Si(Me_4C_5)^tBuNTiMe_2$ were prepared according to known procedures.

Physical and Analytical Measurements.

NMR spectra were recorded on either Varian VXR 300 (FT 300 MHz, $^1H$; 75 MHz, $^{13}C$) or Varian Gemini-300 (FT 300 MHz, $^1H$; 75 MHz, $^{13}C$; 282 MHz, $^{19}F$) instruments. Chemical shifts for $^1H$ and $^{13}C$ spectra were referenced using internal solvent resonances and are reported relative to tetramethylsilane. $^{19}F$ NMR spectra were referenced to external $CFCl_3$. NMR experiments on air-sensitive samples were conducted in Teflon valve-sealed sample tubes (J. Young). Melting temperatures of polymers were measured by DSC (DSC 2920, TA Instruments, Inc.) from the second scan with a heating rate of 20° C./min.

EXAMPLE 1

Trityl Perfluorobiphenyl Aluminate, $Ph_3C^+PBA^-$.

n-Butyllithium (1.6M in hexanes, 25 mL, 40 mmol) was added dropwise to bromopentafluorobenzene (18.0 g, 9.1 mL, 72.9 mmol) in 100 mL of diethyl ether cooled by a cold-water bath. The mixture was then stirred for a further 12 h at room temperature. Removal of the solvent followed by vacuum sublimation at 60°–65° C./$10^{-4}$ Torr gave 12.0 g of 2-bromononafluorobiphenyl as a white crystalline solid. Yield: 83.3%. $^{19}F$ NMR ($C_6D_6$, 23° C.): −126.77 (d,$^3J_{F-F}$=25.4 Hz, 1 F, F-3), −135.13 (d, $^3J_{F-F}$=18.9 Hz, 1 F, F-6), −138.85 (d, $^3J_{F-F}$=17.2 Hz, 2 F, F-2'/F-6'), −148.74 (t, $^3J_{F-F}$=20.8 Hz, 1 F, F-4) −150.13 (t, $^3J_{F-F}$=21.7 Hz, 1 F, F-4'), −154.33 (t, $^3J_{F-F}$=21.4 Hz, 1 F, F-5), −160.75 (t, $^3J_{F-F}$=23.9 Hz, 2 F, F-3'/F-5').

To the above 2-bromononafluorobipyhenyl (8.29 g, 21.0 mmol) in a mixed solvent of 70 mL of diethyl ether and 70 mL of pentane was gradually added 13.2 mL of n-butyllithium (1.6M in hexanes, 21.0 mmol) at −78° C. The mixture was stirred for an additional 2 h, and aluminum trichloride (0.67 g, 5.0 mmol) was then quickly added. The mixture was stirred at −78° C. for 1 h and the temperature was then allowed to slowly rise to room temperature. A white suspension resulted after stirring for an additional 12 h. The mixture was filtered and the solvent removed from the filtrate in vacuo. To the yellow sticky residue was added 100 mL of pentane and the mixture was stirred for 1 h. The resulting white solid was collected by filtration and dried in vacuo to give 3.88 g of $Ar^F_3F Al^-Li^+\cdot OEt_2$: yield: 72.4% $^1H$ NMR ($C_7D_8$, 23° C.): 2.84 (q,J=7.2 Hz, 4 H, 2-$CH_2O$), 0.62 (t, J=7.2 Hz, 6 H, 2$CH_3CH_2O$—). $^{19}F$ NMR ($C_6D_6$, 23° C.): −122.80 (s, br, 3 F, F-3), −134.86 (s, 3 F, F-6), −139.12 (s, 6 F, F-2'/F-6'), −153.95 (t, $^3J_{F-F}$=18.3 Hz, 3 F, F-4), −154.52 (t, $^3J_{F-F}$=20.2 Hz, 6 F, F-4'/F-5), −162.95 (s, 6 F, F-3'/F-5'), −176.81 (s, br, 1 F, Al—F). The above lithium salt (1.74 g, 1.62 mmol) and $Ph_3CCl$ (0.48 g, 1.72 mmol) was suspended in pentane and stirred overnight and the resulting orange solid was collected by filtration and washed with pentane. The crude product was then redissolved in $CH_2Cl_2$ and filtered through Celite to remove LiCl, followed by pentane addition to precipitate the orange solid. Recrystallization from $CH_2Cl_2$/pentane at −78° C. overnight gave 1.56 g orange crystals of the title compound. Yield: 70.5%. Analytical and spectroscopic data for PBA are as follows: $^1H$ NMR ($CDCl_3$, 23° C.): 8.25 (t, J=7.5 Hz, 3 H, p-H, Ph), 7.86 (t, J=7.5 Hz, 6 H, m-H, Ph), 7.64 (dd, J=8.4 Hz, J=1.2 Hz, 6 H, o-H, Ph), 1.28 (m), 0.88(t) (pentane residue). $^{19}F$ NMR ($CDCl_3$, 23° C.): −121.05 (s, 3 F, F-3), −139.81 (s, 3 F, F-6), −141.19 (s, 6 F, F-2'/F-6), −156.93 (t, $^3J_{F-F}$=18.3 Hz, 6 F, F-4/F-4'), −158.67 (s, 3 F, F-5). −165.32 (s, 6 F, F-3'/F-5'), −175.60 (s, br, 1 F, Al—F). Anal. Calcd for $C_{60}H_{15}AlF_{28}\cdot C_5H_{12}$: C, 57.12; H, 1.99. Found: C, 57.16; H, 1.43.

EXAMPLE 2

$Cp_2ZrCH_2Ph^+(PBA)^-$ (1).

$Cp_2Zr(CH_2Ph)_2$ (0.081 g, 0.20 mmol) and $Ph_3C^+PBA^-$ (0.261 g, 0.20 mmol) were charged in the glove box into a 25-mL reaction flask with a filter frit and the flask was reattached to the high vacuum line. Toluene (15 mL) was then vacuum-transferred into this flask at −78° C. The mixture was slowly allowed to warm to room temperature and stirred for 4 h. The volume of toluene was next reduced to 5 mL and 10 mL of pentane was condensed into the flask at −78° C. A suspension which formed was quickly filtered and the orange crystalline solid which collected was dried under vacuuum overnight. Yield, 0.22 g (84.4%). Large orange crystals were obtained by slow cooling a pentane solution of the compound to −20° C. over a period of several days. $^1H$ NMR ($C_6D_6$, 23° C.): 6.95 (t, J=7.8 Hz, 2 H, m-H, Ph), 6.80 (t, J=7.5 Hz, 1 H, p-H, Ph), 6.46 (d, J=7.2 Hz, 2 H, o-H, Ph), 5.45 (s, 5 H, Cp), 5.42 (s, 5 H, Cp), 2.47 (d, J=11.4 Hz, 1 H, —$CH_2$), 1.92 (d, J=11.4 Hz, 1 H, —$CH_2$). $^{19}F$ NMR ($C_6D_6$, 23° C.): −117.09 (t, $^3J_{F-F}$=20.5 Hz, 3 F), −133.17 (t, $^3J_{F-F}$=15.2 Hz, 3 F), −138.60 (d, $^3J_{F-F}$=27.3 Hz, 3 F), −139.53 (t, $^3J_{F-F}$=21.2 Hz, 3 F), −146.34 (s, br, 1 F, Al—F), −152.01 (t, $^3J_{F-F}$=24.3 Hz, 3 F), −153.15 (t, $^3J_{F-F}$=20.9 Hz, 3 F), −153.92 (t, $^3J_{F-F}$=18.3 Hz, 3 F), −160.82 (d, $^3J_{F-F}$=21.4 Hz, 3 F), −162.52 (t, $^3J_{F-F}$=24.53 Hz, 3 F), $^{13}C$ NMR ($C_7D_8$, 23° C.): 129.20 (d,$^3J_{CH}$=156.2 Hz, Ph), 128.26 (d, $^3J_{CH}$=157.1 Hz, Ph), 127.52 (s, ipso-Ph), 125.42 (d, $^3J_{CH}$=158.1 Hz, Ph), 114.77 (d, $^3J_{CH}$=176.5 Hz, Cp), 66.68 (t, $^3J_{CH}$=122.8 Hz, —$CH_2$), Anal. Calcd for $C_{53}H_{17}AlF_{28}Zr$: C, 48.82; H, 1.31. Found: C, 48.77; H, 1.36.

EXAMPLE 3

$Cp''_2ZrMe^+ PBA^-$ (2).

The procedure is the same as that of synthesis of Example 1 above. Yield: 81.7%. $^1H$ NMR ($C_2D_2Cl_4$, 23° C.): δ 5.95 (s, br, 1 H, $C_5H_3Me_2$), 5.77 (s, br, 1 H, C5H3Me2), 5.72 (s, br, 1 H, ($C_5H_3Me_2$), 5.46 (s, br, 1 H, $C_5H_3Me_2$), 5.70 (s, br, 1H, $C_5H_3Me_2$), 5.40 (s, br, 1 H, $C_5H_3Me_2$), 2.11 (s, 3 H, $C_5H_3Me_2$), 1.98 (s, 3 H, $C_5H_3Me_2$), 1.76 (s, 3 H, $C_5H_3Me_2$), 1.70 (s, 3 H, $C_5H_3Me_2$), 0.28 (d, $^1J_{CH}$=120.3 Hz, Zr—$^{13}CH_3$). $^{19}F$ NMR ($C_2D_2Cl_4$, 23° C.) is similar to the product of Example 1 except for a different chemical shift for the bridging F at −143.38 ppm. Anal. Calcd for $C_{51}H_{21}AlF_{28}Zr$: C, 47.71; H, 1.65. Found: 47.46; H, 1.37.

EXAMPLE 4

$C_5H_3(SiMe_3)_2ZrMe^+PBA^-$ (3).

This complex was prepared as described in Example 1 above. It decomposes in toluene solution within 2 h at 25° C. and undergoes rapid decomposition to a myriad of unidentified products at higher temperatures. Characterization of the complex is based on very clean NMR scale reactions. This complex was generated in situ for polymerization studies. $^1H$ NMR $C_7D_8$, 23° C.): δ 6.88 (s, br, 1 H, $C_5H_3TMS_2$), 6.71 (t, J=2.1 Hz, 1 H, $C_5H_3TMS_2$), 6.31 (s, br, 1 H, $C_5H_3TMS_2$), 6.23 (s, br, 1 H, $C_5H_3TMS_2$), 5.79 (s, br, 1 H, $C_5H_3TMS_2$), 5.71 (s, br, 1 H, $C_5H_3TMS_2$), 0.70 (s, br, 3 H, Zr—$CH_3$). 0.17 (s, 3 H, $C_5H_3TMS_2$), 0.10 (s, 3 H, $C_5H_3TMS_2$), −0.05 (s, 3 H, $C_5H_3TMS_2$), −0.07 (s, 3 H, $C_5H_3TMS_2$). $^{19}F$ NMR ($C_7D_8$, 23° C.): δ −112.12 (d, $^3J_{F-F}$=12.2 Hz, 3 F), −133.22 (t, $^3J_{F-F}$=15.5 Hz, 3 F), −137.49 (s, 3 F), −138.40 (t, $^3J_{F-F}$=21.7 Hz, 3 F), −144.23 (s, br, 1 F, Al—F), −153.41 (m, 6 F), −154.15 (t, $^3J_{F-F}$=21.2 Hz, 3 F), −161.80 (d, $^3J_{F-F}$=18.3 Hz, 3 F), −162.82 (t, $^3J_{F-F}$=21.4 Hz, 3 F).

EXAMPLE 5

$(Cp'_2ZrMe^+(PBA))^-$ (4) is too thermally unstable at 25° C. to isolate. The $^1H$ NMR monitored reaction of $Cp'_2ZrMe_2$ and $Ph_3C^+PBA^-$ in $C_2D_2Cl_4$ clearly reveals the formation of $Ph_3CCH_3$ (δ 2.15) and a broad singlet at δ 0.25 assignable to the $ZrCH_3^+$ group. More than 4 Cp methyl resonances at δ 1.97–1.72 ppm with different intensities are observed indicating the decomposition. Complex 4 was generated in situ for polymerization studies. $^{19}F$ NMR ($C_2D_2Cl_4$): δ −114.77 (s, br, 3 F), −132.11 (t, $^3J_{F-F}$=15.2 Hz, 3 F), −136.84 (t, $^3J_{F-F}$=22.0 Hz, 3 F), −137.29 (s, br, 3 F), −150.90 (t, $^3J_{F-F}$=20.9 Hz, 3 F), −151.85 (t, $^3J_{F-F}$=23.9 Hz, 3 F), −152.47 (t, $^3J_{F-F}$=24.5 Hz, 3 F), −155.78 (s, br, 1 F Al—F), −160.02 (d, $^3J_{F-F}$=16.5 Hz, 3 F), −161.06 (t, $^3J_{F-F}$=21.2 Hz, 3 F).

EXAMPLE 6

$Me_2Si(^tBuN)(C_5Me_4)ZrMe^+PBA^-$.

$Me_2Si(Me_4C_5)(^tBuN) ZrMe_2$ (0.148 g, 0.4 mmol) and $Ph_3C^+ PBA^-$ (0.523, 0.4 mmol) were reacted in the same manner as in Example 1 to yield 0.35 g of the above complex as a white crystalline solid. Yield: 64.8%. The complex is quite soluble in pentane and cold pentane was used to wash the product. $^1H$ NMR ($C_7D_8$, 23° C.): δ 1.98 (s, 3 H, $C_5Me_4$), 1.82 (s, 3 H, $C_5Me_4$), 1.76 (s, 3 H, $C_5Me_4$), 1.27 (s, 3 H, $C_5Me_4$), 0.93 (s, 9 H, N-tBu), 0.24 (s, 3 H, $SiMe_2$), 0.18 (s, 3 H,Zr—$CH_3$), 0.15 (s, 3 H, $SiMe_2$), $^{19}F$ NMR ($C_7D_8$, 23° C.) δ −108.92 (s, br, 1 F, Al—F), −117.26 (s, br, 3 F), −133.19 (t, $^3J_{F-F}$=12.1 Hz, 3 F), −139.25 (s, 6 F), −152.53 (t, $J_{F-F}$=21.2 Hz, 3 F), −153.00 (d, $^3J_{F-F}$=21.2 Hz, 3 F), −153.00 (d, $^3J_{F-F}$=21.4 Hz, 3 F), −153.76 (t, $^3J_{F-F}$=24.3 Hz, 3 F), −160.94 (t, $^3J_{F-F}$=22.6 Hz, 3 F), −162.80 (t, $^3J_{F-F}$=21.4 Hz, 3 F). $^{13}C$ NMR ($c_7D_8$, 23° C.): δ 130.19 ($C_5Me_4$), 129.09 ($C_5Me_4$), 127.18 ($C_5Me_4$), 126.44 ($C_5Me_4$), 124.33 ($C_5Me_4$), 56.63 (N-$CMe_3$), 38.58 (q. J=120.6 Hz, N-$CMe_3$), 32.70 (q. J=120.8 Hz, Zr—$CH_3$), 15.75 (q, J=127.9 Hz, $C_5Me_4$), 14.05 (q, J=128.0 Hz, $C_5Me_4$), 12.00 (q, J=127.8 Hz, $C_5Me_4$), 10.18 (q, J=128.1 Hz, $C_5Me_4$), 8.49 (q, J=121.0 Hz, $SiMe_2$), 6.52 (q, J=120.9 Hz, $SiMe_2$). Anal Calcd for $C_{52}H_{30}AlF_{28}NSiZr$: C, 46.37; H, 2.25; N, 1.04. Found: C, 46.65; H, 2.13; N, 0.89.

EXAMPLE 7

$Me_2Si(Me_4C_5)(^tBuN) TiMe^+PBA^-$. $Me_2Si(Me_4C_5)(tBuN) TiMe_2$ (0.065 g, 0.2 mmol) and $Ph_3C^+ PBA^-$ (0.261, 0.2 mmol) were reacted in the same manner as in Example 1 to yield 0.12 g of the above complex as a yellow crystalline soldi. Yield: 46.0%. Due to its good solubility in pentane, a significant amount of the product remained in the filtrate, resulting in a low isolated yield. An NMR scale reaction indicates the formation of the compound in quantitative yield when the isolation is not required. $^1H$ NMR ($C_6D_6$, 23° C.): δ 2.01 (s, 3 H, $C_5Me_4$), 1.72 (s, 3 H, $C_5Me_4$), 1.61 (s, 3 H, $C_5Me_4$), 1.20 (s, 3 H, $C_5Me_4$), 0.93 (s, 9 H, N-tBu), 0.75 (d, J=3.9 Hz, 3 H), 0.21 (s, H), 0.06 (s, 3 H). $^{19}F$ NMR is similar to that of 3 except slightly different chemical shifts. Anal. Calcd for $C_{52}H_{30}AlF_{28}NSiTi$: C, 47.91; H, 2.32; N, 1.07. Found: C, 47.47; H, 1.96; N, 0.87.

EXAMPLE 8

Synethesis of $Me_2Si(Ind)_2ZrMe^+PBA^-$.

$Me_2Si(Ind)_2ZrMe_2$ (0.082 g, 0.20 mmol) and $Ph_3C^+PBA^-$ (0.261, 0.20 mmol) were reacted in the same manner as for the synthesis of 1 above to yield 0.19 g of the title complex as an orange crystalline solid. Yield: 68.6%. Two diastereomers are found in a 1.3:1 ratio. $^1H$ NMR ($C_6D_6$, 23° C.) for diastereomer A (56%): δ 7.45 (d, J=8.7 Hz, 1 H, $C_6$-H0, 7.27–6.88 (m, 4 H, $C_6$-H), 6.67 (t, J=7.5 Hz, 2 H, $C_6$-H), 5.88 (t, J=7.5 Hz, 1 H, $C_6$-H), 6.82 (t, J=3.3 Hz, 1 H, $C_5$-β H), 5.96 (d, J=3.3 Hz, 1 H, $C_5$-β H), 5.69 (s, br, 1 H, $C_5$-α H), 5.19 (d, $J_{HF}$=2.1 Hz, 3 H,Zr—$CH_3$). Diastereomer B (44%): δ 7.94 (d, J=8.7 Hz, 1 H, $C_6$-H), 7.27–6.88 (m, 4 H, $C_6$-H), 6.58 (t, J=7.5 Hz, 2 H, $C_6$-H), 5.79 (t, J=7.5 Hz, 1 H, $C_6$-H), 6.42 (d, J=3.3 Hz, 1 H, $C_5$-β H), 5.85 (d, J=3.3 Hz, 1 H, $C_5$-β H), 5.56 (s, br, 1 H, $C_{5-α}$ H), 4.80 (d, J=3.3 Hz, 1 H, $C_5$-α H), 0.46 (s, 3 H, $SiMe_2$), 0.25 (s, 3 H, $SiMe_2$), −0.64 (d, $J_{HF}$=2.1 Hz, 3 H, Zr—$CH_3$). $^{19}F$ NMR ($C_6D_6$, 23° C.) for diastereomer A (56%): δ −115.86 (s, br, 3 F), −132.23 (s, br, 1 F, Al—F), −133.76 (t, $^3J_{F-F}$=18.3 Hz, 3 F), −138.53 (s, br, 3 F), −139.40 (t, $^3J_{F-F}$ 18.3 Hz, 3 F), −153.10 (t, $^3J_{F-F}$=18.3 Hz, 3 F), −153.44 (t, $^3J_{F-F}$=18.3 Hz, 3 F), −154.72 (t, $^3J_{F-F}$=21.2 Hz, 3 F), −161.18 (t, $^3J_{F-F}$=18.3 Hz, 3 F), −162.86 (t, $^3J_{F-F}$=18.3 Hz, 3 F). Diastereomer B (44%): δ −113.48 (s, br, 3 F), −133.76 (t, $^3J_{F-F}$=21.2 Hz, 3 F), −134.44 (s, br, 1 F, Al—F), −137.89 (s, br, 3 F), −139.09 (t, $^3J_{F-F}$=18.3 Hz, 3 F), −153.10 (t, $^3J_{F-F}$=18.3 Hz, 3 F), −153.28 (t, $^3J_{F-F}$=18.3 Hz, 3 F), −153.73 (t, $^3J_{F-F}$=18.3 Hz, 3 F), −161.03 (t, $^3J_{F-F}$=18.3 Hz, 3 F), −162.68 (t, $^3J_{F-F}$=18.3 Hz, 3 F). $^{13}C$ NMR ($C_6D_6$, 23° C.): δ 134.02, 132.96, 132.43, 128.31, 127.67, 127.28, 126.95, 126.64, 126.21, 125.90, 125.81, 124.88, 124.20, 124.10, 123.57, 122.89, 122.01, 121.98 ($C_6$-ring), 119.16, 116.56, 115.96, 114.94, 112.90, 112.79 ($C_5$-ring), 91.82, 90.95, 89.30, 89.20, ($C_5$-Si), 51.46, 51.73, (Zr—$CH_3$), −1.31, −2.13, −2.88, −3.51 ($SiMe_2$). Anal. Calcd for $C_{57}H_{21}AlF_{28}SiZr$: C, 49.47; H, 1.53. Found: C, 49.09; H, 1.27.

EXAMPLES 9–15

Ethylene and Propylene Polymerization.

In a glove box, a 250 mL flamed, 3-necked round-bottom flask equipped with a magnetic stirring bar was charged with metallocene (5–10 mg) and cocatalyst $Ph_3C^+ PBA^-$, in a 1:1 molar ratio and the flask was then reattached to the high vacuum line. A measured amount of dry toluene (50 mL for this study) was next condensed onto the solids and the mixture was warmed to room temperature with stirring for 10 min to preactivate the catalyst. The resulting solution was then equilibrated at desired reaction temperature using an external constant temperature bath. Gaseous ethylene or propylene was next introduced with rapid stirring and the pressure was maintained at 1.0 atm by means of a mercury bubbler. After a measured time interval, the reaction was quenched by the addition of 2% acidified methanol. The polymer was collected by filtration, washed with methanol, and dried on high vacuum line overnight to a constant weight. Highly isotactic polypropylene is the result of propylene polymerization using $PBA^-$ as a catalyst. The reaction parameters and results are set forth in the Table.

TABLE

Ethylene Polymerization Activities with Metallocene/$Ph_3C^+ PBA^-$ Catalysts and Polymer Properties

| Example No. | catalyst | Tp (°C.) | μmol of cat. | reaction time (min) | polymer yields (g) | activity[a] (g of polymer/(mol of cat · amt · h) | $M_w$[c] | Mw/Mn | $T_m$[d] (°C.) | $ΔH_u$ (cal/g) |
|---|---|---|---|---|---|---|---|---|---|---|
| 5. | $Cp_2ZrMe_2$ | 25 | 20 | 20 | 0 | 0 | | | | |
| 6. | $Cp''_2ZrMe_2$ | 25 | 20 | 30 | 0.18 | $1.80 × 10^4$ | $5.46 × 10^5$ | 6.0 | 139.4 | 40.5 |
| 7. | $(Cp^{TMS}_2)_2ZrMe_2$ | 25 | 15 | 2.0 | 0.54 | $1.08 × 10^6$ | $1.26 × 10^6$ | 5.6 | 142.3 | 29 |

TABLE-continued

Ethylene Polymerization Activities with Metallocene/Ph₃C⁺ PBA⁻ Catalysts and Polymer Properties

| Example No. | catalyst | Tp (*C.) | μmol of cat. | reaction time (min) | polymer yields (g) | activity[a] (g of polymer/(mol of cat · amt · h) | $M_w$[c] | Mw/Mn | $T_m$[d] (°C.) | $\Delta H_u$ (cal/g) |
|---|---|---|---|---|---|---|---|---|---|---|
| 8. | Cp'₂ZrMe₂ | 25 | 15 | 0.67 | 1.15 | $6.90 \times 10^6$ | $8.97 \times 10^4$ | 4.6 | 138.0 | 53.9 |
| 9. | CGCZrMe₂ | 25 | 15 | 10 | 0 | 0 | | | | |
| 10. | CGCTiMe₂ | 60 | 30 | 30 | 0.20 | $1.33 \times 10^4$ | $2.05 \times 10^6$ | 3.9 | 139.2 | 19.5 |
| 11. | CGCTiMe₂ | 110 | 30 | 5.0 | 0.20 | $8.00 \times 10^4$ | $2.05 \times 10^6$ | 3.1 | 142.5 | 24.4 |
| 12.[e] | rac-Me₂Si(Ind)₂ZrMe⁺PBA⁻ | 60 | 20 | 120 | 0.65 | $1.63 \times 10^4$ | $2.34 \times 10^4$ | 3.59 | 145 | — |

[a]Carried out at 1 atm of ethyelene and 50 mL of toluene on high vacuum line
[b]Reproducibility between runs = 10–15%
[c]GPC relative to polystyrene standards
[d]DSC from the second scan
[e]For propylene polymerization The table summarizes ethylene polymerization activities by various metallocene catalysts activated with PBA⁻. Cp₂ZrMe₂ exhibits virtually no activity for ethylene polymerization. This is presumably caused by the anion coordination through a Zr—F—Al bridge (FIG. 2a). However, as the ligand framework of the cation portion changes from Cp (C₅H₅), to Cp"(1,2,-Me₂C₅H₃), to [1,3-(SiMe₃) ₂C₅₃], to Cp'(C₅Me₅), the activity for ethylene polymerization increases dramatically (Examples 1–4) and reaches the highest level of $6.90 \times 10^6$ g of PE/(mole of cat-atm-h) with the Cp'₂ZrMe₂ catalyst (Example 4). The polyethylene produced is highly linear with melting temperature $T_m$ of 139.4° C. and crystalline with heat of fusion $\Delta H_u$ of 53.9 cal/g. As the bulkiness of cation portion increases, the degree of anion coordination drops significantly, clearly reflecting the relationship between the polymerization activity and the relative tightness of cation-anion pairing structure.

In the case of the Cp' ligand, the separation of cation and anion reaches an optimum condition for reactivity that results in the maximum polymerization activity and instability of the cationic complex derived therefrom as well. Such a dramatic influence of the ligand framework substituents on polymerization activity is unprecedented and suggests the special features of the subject anion. PBA is apparently such a large anion that separation of anion and cation can be easily and substantially tuned and optimized by selecting the appropriate bulky cation.

For the sterically more accessible CGC type of catalyst, PBA⁻ promotes no catalytic activity at room temperature, resulting from the strong anion coordination as reflected by the 66 ppm down-field shift of the Al—F F resonance as compared to PBA⁻ (FIG. 2c, Example 5). However, as the temperature of polymerization increases, the polymerization activity increases dramatically (Examples 5–7) presumably due to a higher degree of separation of cation-anion pairs at higher temperatures.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed is:

1. A catalytic complex of the formula: (CpCp'MR)⁺ AR'R"R'"F⁻ where
   Cp and Cp' is each a group containing a cyclopentadienyl ligand
   M is Ti, Zr, Hf, Th, or U
   R is an alkyl or aryl group (C≦20), or hydride
   A is Al, Ga, or In
   R', R", and R'" is each a fluorinated phenyl, fluorinated biphenyl or fluorinated polycyclic fused ring group.

2. The complex of claim 1, wherein said cyclopentadienyl ligand is selected from the group consisting of indenyl, $\eta^5$-C₅H₅; $\eta^5$-1,2-Me₂C₅H₃; $\eta^5$-1,3-(SiMe₃)₂ C₅H₃; $\eta^5$-C₅Me₅ and Me₂Si($\eta^5$-Me₄C₅)('BuN).

3. The complex of claim 1 wherein said polycyclic fused ring groups are naphthyl, anthracenyl, or fluorenyl.

4. A method of preparing a catalyst composition including the step of adding tris(2', 2", 2'"-nonafluorobiphenyl fluoroaluminate to a cationic metallocene.

5. The method of claim 4, wherein said cationic metallocene incorporates a cyclopentadienyl ligand.

6. The method of claim 4, wherein said cationic metallocene incorporates ligands selected from the group consisting of indenyl, $\eta^5$-C₅H₅; $\eta^5$- 1,2-Me₂C₅H₃; $\eta^5$-1,3-(SiMe₃)₂ C₅H₃; $\eta^5$-C₅Me₅ and Me₂Si($\eta^5$-Me₄C₅)('BuN).

7. A method of polymerizing an alpha olefin comprising the step of adding the catalyst (CpCp'MR)⁺ AR'R"R'"F⁻ to the alpha olefin where
   Cp and Cp' is each a group containing a cyclopentadienyl ligand
   M is Ti, Zr, Hf, Th, or U
   R is an alkyl, or aryl group (C≦20), or hydride
   A is Al, Ga, or In
   R', R", and R'" is each a Fluorinated phenyl, fluorinated biphenyl or fluorinated polycyclic fused ring group.

8. The method of claim 7, wherein said alpha olefin is selected from the group consisting of ethylene, propylene and styrene.

9. The method of claim 7, wherein said cyclopentadienyl ligand is selected from the group consisting of indenyl, $\eta^5$-C₅H₅; $\eta^5$-1,2-Me₂C₅H₃; $\eta^5$-1,3-(SiMe₃)₂ C₅H₃; $\eta^5$-C₅Me₅ and Me₂Si($\eta^5$-Me₄C₅)('BuN).

10. The method of claim 7 wherein said reaction is carried out at ambient conditions.

11. The method of claim 7, wherein said reaction is initiated at temperatures from 25° C. to 110° C.

* * * * *